US006667164B1

(12) United States Patent
Miller et al.

(10) Patent No.: US 6,667,164 B1
(45) Date of Patent: Dec. 23, 2003

(54) METHOD FOR DETERMINING THE MHC GENOTYPE OF CHICKENS

(75) Inventors: Marcia M. Miller, Altadena, CA (US); Marielle Afanassieff, Le Peage de Roussillon (FR); W. Elwood Briles, Sycamore, IL (US)

(73) Assignees: The Board of Trustees for Northern Illinois University, DeKalb, IL (US); City of Hope, Duarte, CA (US)

( * ) Notice: Subject to any disclaimer, the term of this patent is extended or adjusted under 35 U.S.C. 154(b) by 0 days.

(21) Appl. No.: 09/619,758

(22) Filed: Jul. 19, 2000

Related U.S. Application Data

(60) Continuation-in-part of application No. 09/244,093, filed on Feb. 4, 1999, now Pat. No. 6,242,182, which is a division of application No. 08/774,025, filed on Dec. 27, 1996, now Pat. No. 5,944,652.

(51) Int. Cl.[7] .................. C12Q 1/68; C12P 19/34; C07H 21/04; A61K 49/00

(52) U.S. Cl. ................ 435/91.2; 435/6; 536/23.53; 536/24.31; 424/9.21

(58) Field of Search ................ 435/6, 91.2; 536/23.53, 536/24.31; 424/9.21; 119/174; 800/8

(56) References Cited

U.S. PATENT DOCUMENTS

| | | | |
|---|---|---|---|
| 5,451,670 A | 9/1995 | Miller | 536/24.31 |
| 6,218,106 B1 * | 4/2001 | Miller et al. | 435/6 |
| 6,242,182 B1 * | 6/2001 | Miller et al. | 435/6 |

FOREIGN PATENT DOCUMENTS

| | | | |
|---|---|---|---|
| EP | 0866 135 A2 | 9/1998 | |
| EP | 0866 135 A3 | 9/1998 | |
| WO | 9927132 | 11/1998 | C12Q/1/68 |
| WO | WO 01 94615 A2 | 12/2001 | |

OTHER PUBLICATIONS

Luna, Manual of Histologic Staining Methods of the Armed Forces Institute of Pathology, 3rd Ed., McGraw–Hill Book Co., New York, pp. 32–46 (1968).
Kaufman et al., The "Minimal Essential MHC" revisted: Both peptide–binding and cell surface expression level of MHC molecules are polymorphisms selected by pathogens in chickens, Hereditas 127:67–73 (1997).
Bacon, L.D. and Witter, R.L., *Avian Diseases*, 36:378–85 (1992).
Bacon, L.D. and Witter, R.L., *J. Hered.*, 86:269–73 (1995).
Wittzell, H. et al., *Immunogenetics*, 42:68–71 (1995).
Jarvi, S.I. et al., *Immunogenetics*, 43:125–135 (1996).
Miller, M.M. et al., *Proc. Nat'l. Acad. Sci. USA*, 93:3958–3962 (1996).
Kroemer, G. et al., *Immuunogenetics*, 31:405–409 (1990).

Blasczyk et al., "Complete subtyping of the HLA–A locus by sequence–specific amplification followed by direct sequencing or single–strand conformation polymorphism analysis" *Tissue Antigens*, 46:86–95 (1995).
Schat, K.A. et al., *Avian Pathol.*, 11:593–605 (1982).
Briles, W.E. et al., *Genetics*, 35:633–652 (1950).
Pink, J.R.L. et al., *Immunogenetics*, 5:203 (1977).
Guillemot, F. et al., *EMBOJ*, 7:2775–85 (1988).
Lamont, S.J. et al., *Poult. Sci.*, 69:1195 (1990).
Shuman, R.M. et al., "Development of an Mhc Typing Test Using DNA Amplification and Oligonucleotide Probes" *Poult. Sc.*, 72 (Suppl. 1):10 (Abstr.) (1993).
Miller, M.M. and Goto, R.M., "PCR–SSCP: a method for studying the polymorphism of the B–G antigens of the chicken major histocompatibility complex" *Avian Immunology in Progress*, Tours (France), Aug. 31–Sep. 2, 1993, Ed. INRA, Paris 1993 (Les Colloques, No. 62).
Briles, W.E. et al., "A polymorphic system related to but genetically independent of the chicken major histocompatibility complex" *Immunogenetics*, 37:408–414 (1993).
Miller, M.M. et al., "Two Mhc class I and two Mhc class II genes map to the chicken Rfp–Y system outside the B complex" *Proc. Nat'l. Acad. Sci. USA*, 91:4397–4401 (1994).
Zoorob, R. et al., *Eur. J. Immunol.*, 23:1139–45 (1993).
Aeed et al., "Influence of different B–complex recombinants on the outcome of *Rous sarcomas* in chickens" Animal Genetics 24:177–181 (1993).
Juul–Madsen et al., "New chicken Rfp–Y haplotypes on the basis of MHC class II RFLP and MLC analyses," Immunogenetics 45:345–352 (1997).
Lamont, "The chicken major histocompatibility complex and disease," Rev. sci. tech. Off. int. Epiz. 17(1):128–142 (1998).
Oto et al., "Optimization of nonradioistopic single strand conformation polymorphism analysis with a conventional minislab gel electrophoresis apparatus" Analytical Biochemistry 213:19–22 (1993).
Pharr et al., Histocompatibility antigen(s) linked to Rfp–Y (Mhc–like) genes in the chicken, Immunogenetics 45:52–58 (1996).
Plachý et al., src–specific immunity in inbred chickens bearing v–src DNA–and RSV–induced tumors, Immunogenetics 40:257–265 (1994).
Wakenell et al., "Association between the Rfp–Y haplotype and the incidence of Marek's disease in chickens," Immunogenetics 44:242–245 (1996).

(List continued on next page.)

*Primary Examiner*—Ethan Whisenant
*Assistant Examiner*—Joyce Tung
(74) *Attorney, Agent, or Firm*—Rothwell, Figg, Ernst & Manbeck

(57) ABSTRACT

Disease resistance in domesticated fowl has been associated with the B and Rfp-Y systems of major histocompatability genes. A method for breeding domesticated fowl to produce disease resistant offspring involves selecting at least one parent that has a B genotype, an Rfp-Y genotype or both that is characteristic of disease resistance and mating that parent with a second parent to produce a disease resistant offspring.

2 Claims, 8 Drawing Sheets

OTHER PUBLICATIONS

Orita et al. "Rapid and sensitive detection of point mutations and DNA polymorphisms using the polymerase chain reaction" Genomics 5:874–879 (1989).

Heath, "Developing DNA–Based MHC Typing Reagents for Commercial White Leghorn and Broiler Strains,", Poult. Sci. 73 (Supp 1):5 (1994).

Chaussë et al., "Molecular genotyping of four chicken β–complex haplotypes with B–complex haplotypes with B–L$_β$, B–F, and B–G probes," Immunogenetics 29:127–130 (1989).

Ronald Goto et al., "Isolation of a cDNA clone from the B–G subregion of the chicken histocompatibility (B) complex," Immunogenetics 27:102–109 (1988).

Miller, M.M. et al., "Genotyping chickens for the B–G subregion of the major histocompatibilit complex using restriction fragment length polymorphisms," Immunogenetics 28:374–379 (1988).

Pharr, G.T. et al., "Identification of Rfp–Y (Mhc–like) Haplotypes in Chickens of Cornell Lines N and P," J. Hered. 6:504–512 (1997).

Li et al. "The MHC of a Broiler Chicken Line: Serology, B–G Genotypes, and B–F/B–LB Sequences" *Immunogenetics* 49:215–224 (1999).

Vallejo, R.L. et al., "Non–association between Rfp–Y major histocompatibility complex–like genes and susceptibility to Marek's disease virus–induced tumours in $6_3×7_2$ F$_2$ intercross chickens," Animal Genetics 28:331–337 (1997).

Kaufman et al., "Genes organisation determines evolution of function in the chicken MHC" *Immunological Reviews* 167:101–117 (1999).

Miller et al. "Regions of homology shared by Rfp–Y and major histocompatibility B complex genes" *Immunogenetics* 39:71–73 (1994).

Jarvi et al. "Identification of the major histocompatibility complex in the ring–necked pheasant, Phasianus colchicus" *Animal Genetics* 23:211–220 (1992).

Miller et al. "The RFP–Y system—A second system of histocompatibility genes in the chicken" In: *Advances in Avian Immunology Research* pp. 95–103, Eds. T.F. Davison, N. Burnstead and P. Kaiser, Carfax Publishing Co. (1995).

Afanassieff, M. et al., "Are chicken Rfp–Y class I genes classical or nonclassical," Major Histocompatibility Complex Evolution, Structure and Function, M. Kasahara (Ed.) pp. 236–247 (2000).

Briles, W.E. et al., Genetics, 35:633–652 (1950).

Pink, J.R.L. et al., Immunogenetics, 5:203 (1977).

Guillemot, F. et al., EMBOJ, 7:2775–85 (1988).

Lamont, S.J. et al., Poult. Sci., 69:1195 (1990).

Shuman, R.M. et al., Development of an Mhc Typing Test Using DNA Amplification and Oligonucleotide Probes, Poult, Sc., 72 (Supp. 1):10 (Abstr.) (1993).

Miller, M.M. and Goto, R.M., PCR–SSCP; a method for studying the polymorphism of the B–G antigens of the chicken major histocompatibility complex, Avian Immunology in Progress, Tours (France), Aug. 31–Sep. 2, 1993, Ed. INRA, Paris 1993 (Les Colloques, No. 62).

Briles, W.E. et al., A polymorphic system related to but genetically independent of the chicken major histocompatibility complex, Immunogenetics, 37:408–414 (1993).

Miller, M.M. et al., Two Mhc class * and two Mhc class II genes map to the chicken Rfp–Y system outside the B complex, Proc. Nat'l. Acad. Sci. USA, 91:4397–4401 (1994).

Afanassiff, M. et a., Abstract presented at the Avian Immunology Research Group Meeting, Obergurgal, Austria, Apr. 21–24, 1996.

Bacon, L.D. and Witter, R.L., Avian Diseases, 36:378–85 (1992).

Bacon, L.D. and Witter, R.L., J. Hered., 86:269–73 (1995).

Wittzell, H. et al., Immunogenetics, 42:68–71 (1995).

Jarvi, S.I. et al., Immunogenetics, 43:125–135 (1996).

Miller, M.M. et al., Proc. Nat'l. Acad. Sci. USA, 93:3958–3962 (1996).

Kroemer, G. et al., Immunogenetics, 31:405–409 (1990).

Blasczyk et al., Complete subtyping of the HLA–A locus by sequence–specific amplification followed by direct sequencing or single–strand conformation polymorphism analysis, Tissue Antigens, 46:86–95 (1995).

Briles, W.E. et al. Animal Genetics, 25(Supp. 2):18 (1994).

Schat, K.A. et al., Avian Pathol., 11:593–605 (1982).

Kean et al., "Differences in major histocompatibility complex frequencies after multitrait, idvergent selection for immunocompetance," Poultry Science 73:7–17 (1994).

Davidson et al., "PCR diagnosis of Marek's disease, reticuloendotheliosis and lyumphoid leukosis in chickens and turkeys," PCR: A Diagn. Hum. Anim. Virus Dis., 543–552 (1995).

* cited by examiner

FIG. 6

METHOD FOR DETERMINING THE MHC GENOTYPE OF CHICKENS

CROSS-REFERENCE TO RELATED APPLICATIONS

This application is a continuation-in-part of pending prior application Ser. No. 09/244,093, filed Feb. 4, 1999, now U.S. Pat. No. 6,242,182, which is a divisional of application Ser. No. 08/774,025, filed Dec. 27, 1996, now U.S. Pat. No. 5,944,652.

This invention was funded in part by the United States Department of Agriculture under Federal Assistance Program Agreement No. 58-3148-5-023 and NRICGP 92-37204-8244 and by National Science Foundation Grant No. MCB-9604589. The U.S. government may have certain rights in the invention.

BACKGROUND OF THE INVENTION

1. Field of the Invention

This invention relates to a method for haplotyping and breeding domesticated fowl for increased disease resistance. In one related aspect, the invention relates to a method for determining the Rfp-Y, B-F, B-L and B-G haplotypes of domesticated fowl, including chickens. In a further, related aspect, the invention relates to a method for breeding domesticated fowl raised for meat and eggs to achieve increased disease resistance and vitality.

2. Description of the Background Art

In domesticated fowl, the major histocompatibility complex ("Mhc") which is associated with the regulation of immune recognition and immune response, is called the B system. This system, which comprises polymorphic Mhc Class I (B-F), Mhc Class II (B-L) and B-G genes, has been known to exist since the early 1940's. Briles, W. E. et al., *Genetics*, 35:633–652 (1950), Pink, J. R. L. et al., *Immunogenetics*, 5:203 (1977). Genotyping birds for the B system of histocompatibility has been accomplished by several different kinds of tests. The first, and by far the most commonly used method, is a serological test: hemagglutination of chicken red blood cells with alloantisera. This method requires some prior knowledge of the genetics of the animals and availability of appropriate alloantisera.

The second relies on the patterns of B-G gene restriction fragments revealed in genomic DNA digested with a restriction enzyme and analyzed in Southern hybridization with nucleic acid probes for the B-G genes. See Miller et al., U.S. Pat. No. 5,451,670. An advantage of this approach is that prior knowledge of gene sequences is not necessary. A third method relies on B-F (Class I) and B-L (Class II) gene restriction fragment patterns revealed in genomic DNA digested with several restriction enzymes and analyzed by Southern hybridization with nucleic acid probes for the B-F and B-L genes. See Lamont, S. J. et al., *Poult. Sci.*, 69:1195 (1990). This method may underrepresent the different B-F and B-L alleles present in a population.

A fourth method is based on hybridization of oligonucleotide probes specific for known sequences in the various alleles of the B system Class I gene (gene B-FIV on the physical map of chicken Mhc genes (See Guillemot, F. et al., 1988, supra.)). This method requires knowledge of the sequence of the allele at least in the region to which the probe hybridizes. See Shuman, R. M. et al., "Development of an Mhc Typing Test Using DNA Amplification and Oligonucleotide Probes", *Poult. Sci.*, 72 (Suppl. 1): 10 (Abstr.) (1993). A fifth method, also requiring knowledge of gene sequence, employs antibodies developed to a specific epitope on Class I antigens through expression of recombinant genes in chickens.

The use of a technique known as polymerase chain reaction, single-stranded conformational polymorphism ("PCR-SSCP") to study the expression of B-G genes in non-erythroid tissues has been proposed. Miller and Goto, *Avian Immunology in Progress*, Tours (France), Aug. 31–Sep. 2, 1993, Ed. INRA, Paris 1993 (Les Colloques, No. 62). In this method, short segments of B-G genes of interest are amplified using PCR and radioactive tags. The PCR products are then denatured by heating and applied to a non-denaturing polyacrylamide gel. The single-stranded fragments of the heat-denatured DNA fragments assume secondary conformations determined by their sequences and migrate differently in the polyacrylamide gel during electrophoresis, so as to produce a pattern (or fingerprint) representative of the sequences within the genome in the region of amplification. These were revealed in films exposed to the electrophoretic gels.

Recently, a second system of major histocompatibility genes of the chicken has been discovered. Briles, W. E. et al., *Immunogenetics* 37:408–414 (1993). This system, designated Rfp-Y, consists of at least two Class I genes, three Class II genes and a c-type lectin gene. Miller et al., *Proc. Nat'l. Acad. Sci. USA* 91:4397–4401 (1994); Miller et al., *Proc. Nat'l. Acad. Sci. USA* 93:3958–3962 (1996). Haplotypes of Rfp-Y assort independently from haplotypes of the B system. Briles, W. E. et al., *Immunogenetics* 37:408–414 (1993).

The existence of a second genetically-independent complex of polymorphic histocompatibility genes was unexpected, because Mhc genes are typically considered to be in a single linkage group. Previous studies have suggested that at least one Mhc Class II gene in the B-L βIII gene family, now known to be within Rfp-Y is expressed. Zoorob et al., *Eur. J. Immunol.* 23:1139–45 (1993). Transcripts of an Mhc Class I gene within Rfp-Y were also found in many different tissues. See Afanassieff et al., Abstract presented at the Avian Immunology Research Group Meeting, Obergurgal, Austria, April 21–24, 1996; Afanassieff et al., in Kasahara, ed., *The Major Histocompatibility Complex: Evolution, Structure, and Function*, Springer-Verlag, New York, 2000, pp. 236–247. Nevertheless, the role of the Rfp-Y system in immune mediation of disease resistance and the extent to which genes of the Rfp-Y system are expressed in various cell types has heretofore remained unknown.

SUMMARY OF THE INVENTION

In accordance with the present invention, it has been discovered that the Rfp-Y system exerts an effect on Marek's disease resistance. It has also been discovered that, in some allelic combinations, the influence of the Rfp-Y and B systems on Marek's disease resistance may be additive or interactive. Accordingly, the invention provides a method for determining the haplotype of Rfp-Y and B systems of a domesticated fowl. This method involves obtaining a sample of nucleic acid such as genomic DNA from the fowl which contains a region having a sequence corresponding to an Rfp-Y, B-F, B-L or B-G region of the genome which is subject to allelic variation. B-F, B-L and B-G are all linked genes within the B system. The nucleic acid sample is amplified, and the resulting amplification products are denatured. These denatured amplification products are subjected to non-denaturing electrophoretic separation to produce an electrophoresis pattern that is characteristic of the Rfp-Y or B regions (B-F, B-L, B-G) of the domesticated fowl. In preferred embodiments, the method of the invention employs the polymerase chain reaction to produce amplification products of the Rfp-Y or B region of genomic DNA using primers that bound an allelic sequence in the region. Primers suitable for use in this inventive method bound sequences about 50 to about 500 nucleotides long, or preferably about 100 to about 300 nucleotides long and include those of SEQ ID NOS: 5–19. The invention provides primers of SEQ ID NOS:5–19 which may be used with these methods. The invention also provides methods of selecting and breeding disease-resistant domesticated fowl. Disease-resistant fowl are selected by determining the Rfp-Y or B haplotype of a population of domesticated fowl and correlating the haplotypes with resistance to a disease. Those birds possessing haplotypes correlated for disease resistance are selected for breeding and mated with birds of opposite gender to produce disease-resistant offspring.

BRIEF DESCRIPTION OF THE DRAWINGS

FIG. 5 is a photograph of gels showing the SSCP electrophoretic pattern of polymerase chain reaction products associated with different Mhc B Class IIβ genotypes as indicated. FIG. 5A shows analysis of birds having standard Mhc B haplotypes, while

FIG. 6 is a photograph of a gel showing the SSCP electrophoretic pattern of polymerase chain reaction products associated with different Mhc Rfp-Y Class I genotypes as indicated.

DETAILED DESCRIPTION OF THE INVENTION

Figure 1:
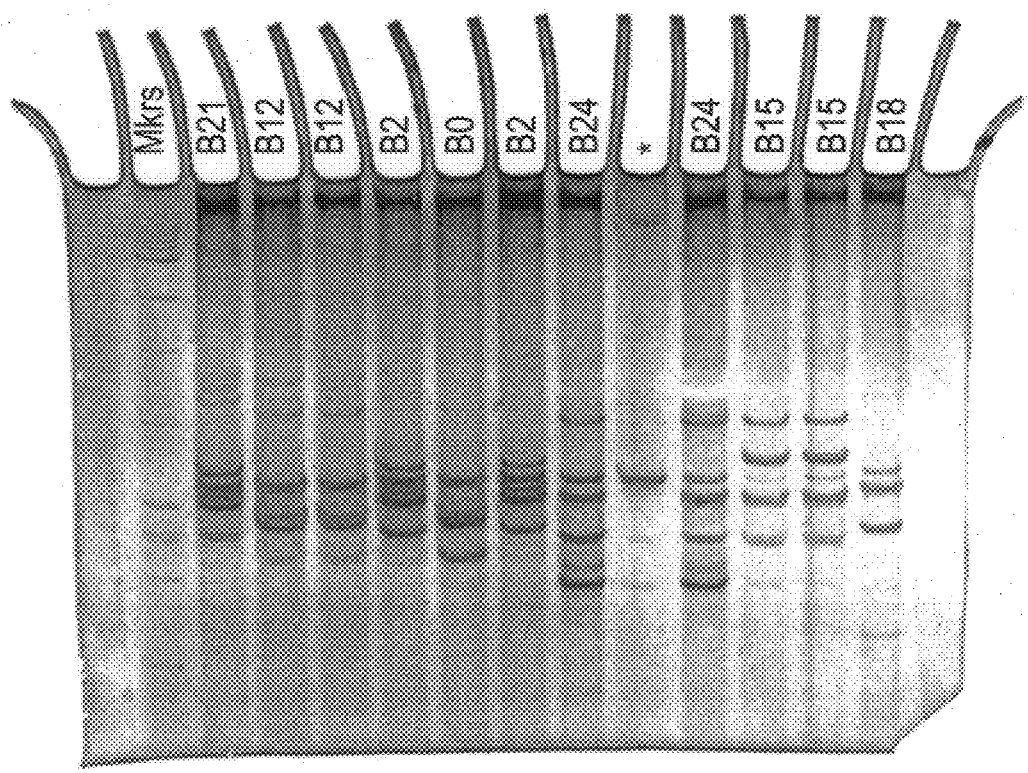
FIG. 1 is a photograph of a gel showing the SSCP electrophoretic pattern of polymerase chain reaction products associated with different Mhc B Class I genotypes as indicated. Mkrs=molecular weight markers. * =non-denatured PCR product.

Breeding programs for domesticated fowl typically are designed to breed disease resistance, as well as numerous other advantageous characteristics, into commercial lines. Marek's disease is of particular interest, in that it is a disease of chickens encountered worldwide. Virtually all commercially grown chickens (there are about thirty-four billion broiler chickens raised annually worldwide) are vaccinated for Marek's disease.

The experimental data described herein indicate that resistance to Marek's disease is influenced by the Rfp-Y haplotype as well as the B system haplotype of domesticated fowl. Pedigree-hatched chicks in families from stock in which three Rfp-Y haplotypes and two B system haplotypes were segregating were challenged with Marek's disease virus ("MDV"). The resulting data demonstrated that both the Rfp-Y and B haplotypes significantly influence the outcome of infection with MDV. Moreover, vaccines are only partially effective, and their effectiveness also is influenced by the B genotype (Bacon, L. D. and Witter, R. L., *Avian Diseases*, 36:378–85 (1992) and Bacon, L. D. and Witter, R. L., *J. Hered.*, 86:269–73 (1995)) and, probably to some degree, the Rfp-Y genotype of the birds.

Genes within B and Rfp-Y both have a demonstrated influence in resistance and susceptability to a number of diseases, including virally-induced tumors, bacterial infections and infections with protozoan parasites. See, for example, Briles et al., *Science* 195:193–195 (1977); Briles et al., *Immunogenetics* 20:217–226 (1984); Longenecker et al., *Immunogenetics* 3:401–407 (1976); Kaufman et al., *Hereditas* 127:67–73 (1997); Wakenell et al., *Immunogenetics* 44:242–245 (1996); Vallejo et al., *Animal Genetics* 28:331–337 (1997); Lamont, *Rev. Sci. Tech.* 17:128–142 (1998); Caron et al., *Poultry Science* 76:677–682 (1997); Facter et al., *J. Virol.* 69:6439–6444 (1995); Uni et al., *Br. Poultry Science* 37:555–561 (1995); Bacon et al., *J. Heredity* 86:269–273 (1995); Hlozanek et al., *Virology* 203:29–35 (1994); Schat et al., *Poultry Science* 73:502–508 (1994); Naki et al., *Avian Disease* 37:1113–1116 (1993); Lamont et al., *Immunogenetics* 25:284–289 (1987); Cotter et al., *Poultry Science* 77:1846–1851 (1998). There are additional studies reported in the literature describing the influence of MHC haplotype in many poultry diseases, for example, the regression of Rous sarcoma virus induced tumors, infectious laryngotracheitis and coccidiosis. See Yoo et al., *Br. Poultry Science* 33:613–620 (1992); Poulsen et al., *Poultry Science* 76 (Suppl. 1):108 abstract (1994); Poulsen et al., *Poultry Science* 77:17–21 (1998); Clare et al., *Immunogenetics* 22:593–599 (1985).

Since the association of MHC haplotype with disease resistance in fowl has been demonstrated, the haplotyping methods described and claimed herein may be used to select for chickens genetically resistant to a variety of diseases. One of the most important diseases of poultry in commercial terms, Marek's disease, is caused by a highly contagious herpes virus that induces T cell lymphomas in chickens. Another disease of consequence in commercially raised domesticated fowl is coccidiosis. Coccidiosis is a protozoan disease of poultry and other birds that results in diarrhea, enteritis and weight loss. MHC haplotype also has been shown to influence resistance, susceptibility and immunity to Eimeria and other commercially important diseases such as laryngotracheitis. Genes located within chicken MHC regions have significant effects on the immune response to pathogens that can be detected experimentally. For example, the capacity of chickens to regress tumors caused by avian leukosis virus is associated with the capacity of T cells to respond to the presentation of MHC restricted antigen. Further associations between MHC haplotype and resistance to two bacterial pathogens (fowl cholera and salmonella are reported).

The previous work of Wakenell et al. indicates that Rfp-Y haplotypes influence resistance to the commercially important Marek's disease in the chicken. Studies of Rfp-Y influence on Marek's disease virus challenge have produced results indicating that Rfp-Y haplotype affects susceptibility to infection in different B complex backgrounds. Wakenell et al., *Immunogenetics* 44:242–245 (1996). In this study, data comparing incidents of Marek's disease tumors in chickens carrying three different Y system genes showed that Rfp-Y system exerts an effect on Marek's disease resistance and that the influence of Rfp-Y haplotypes in some combinations may be quantitatively similar to that of the B-F region.

Methods of chicken haplotyping therefore can be used advantageously to select birds resistant to or with improved immune response upon vaccination to a number of important diseases. Genetic selection for particular MHC haplotypes is valuable to breeders of domesticated fowl for the production of both individuals and flocks that are resistant to numerous diseases.

Thus, determining the Rfp-Y haplotype of domesticated fowl can facilitate breeding programs in which it is desired to breed resistance to Marek's disease and any disease which is influenced by the Mhc into birds raised for meat or eggs. Rfp-Y haplotyping can be accomplished by a variety of procedures, including restriction fragment length polymorphism ("RFLP"), cDNA cloning followed by sequencing, allele-specific oligonucleotide probing and the like. To be used effectively in a breeding program, the haplotyping method should be relatively simple, easy to implement, reliable and fast so that large numbers of samples can be processed quickly and efficiently. A preferred method that meets these requirements is the nucleic acid amplification-SSCP method described below.

To utilize Rfp-Y haplotyping in a commercial breeding program, a database correlating Rfp-Y haplotypes to Marek's or other disease resistance in known breeding lines is created. Breeders can then utilize this database, in conjunction with information about B system Mhc haplotype and other characteristics, in selecting parents. The breeding and haplotyping methods described herein may be used in connection with any species of domesticated fowl that possesses an Rfp-Y Mhc system. The methods are preferably used in breeding programs for domesticated chickens. Evidence of an Rfp-Y system in ring-necked pheasants has been reported. See Wittzell et al., *Immunogenetics* 42:68–71 (1995) and Jarvi et al., *Immunogenetics* 43:125–135 (1996). Data also exists which suggests the presence of an Rfp-Y system in turkeys.

The Rfp-Y region is believed to reside on chicken chromosome 16 (a microchromosome), which also contains the Mhc B region. A genetic map can be postulated for chicken chromosome 16, showing the Rfp-Y system, encompassing two Mhc Class I genes and three Mhc Class II genes, separated from the B system by a region containing the nucleolar organizer region ("NOR") . See Miller et al., *Proc. Nat'l. Acad. Sci. USA* 93:3958–3962 (1996).

The nucleic acid amplification-SSCP haplotyping method of this invention involves amplifying a segment of DNA spanning an allelic region of the Rfp-Y system or the B system. The amplification procedure used may be any method that specifically amplifies the nucleic acid of interest, including polymerase chain reaction ("PCR"), ligase chain reaction, nucleic acid specific base amplification ("NASBA"), and the like. PCR is the preferred amplification procedure.

Genomic DNA, mRNA or cDNA containing a nucleic acid sequence corresponding to the Rfp-Y or B region to be amplified may be used as the sample for the amplification reaction. A genomic DNA sample is preferred.

The segment to be amplified is selected to include one or more allelic regions, so as to produce a unique electrophoretic pattern when subjected to the SSCP procedure. The segment advantageously ranges from about 50 to about 500 nucleotides in length, preferably from about 100 to about 300 nucleotides. Those skilled in the art will recognize that a variety of segments may be selected for amplification.

To be of value in typing for the B and Rfp-Y systems, the segments chosen should be specific for one system or the other so as not to produce patterns from both systems that cannot be distinguished in the electrophoretic patterns. To obtain this specificity, primer sets are chosen that are specific for either the B or the Rfp-Y Class I loci. The primer sets are chosen so that they span a region expected to be polymorphic in these loci yet be specific for either B or Rfp-Y Class I loci or B Class II loci, or B-G loci. For example, the primer set chosen for the B system advantageously hybridizes with sequences within both Class I genes of the B system. In this way if either one or both loci are polymorphic in a particular haplotype the primers will produce DNA amplification products that will provide distinctive electrophoretic patterns. The Class I α-chain genes within the Rfp-Y and the B systems are useful for this approach and the B Class II also appear especially appropriate for the B region tests disclosed herein.

Amplification primers are selected from the sequences of the Rfp-Y and B system Class I, Class II and B-G genes. The two Class I genes of the Rfp-Y system (now designated Y-FV and Y-FVI) and the two Class I genes of the B-F region (designated B-FIV and B-FI) are contained within the cosmids described by Guillemot et al. *EMBO J.* 7:2775–85 (1988) and are identified on the molecular map of the chicken Mhc genes published by those authors. The sequence of the B-FIV gene has been published. Kroemer et al., *Immunogenetics* 31:405–409 (1990). Sequences of other Rfp-Y and B genes contained within the cosmids can be determined by standard procedures. Primers should be specific for each system to allow the amplification of the genes within only one system, Rfp-Y or B. Further, primers are described that are specific for the B Class II and B-G loci, both of which reside in the B region and which are polymorphic.

Following amplification, the amplification products are subjected to single-stranded conformational polymorphism ("SSCP") electrophoretic separation. SSCP has been described in connection with other Mhc genes. See Blasczyk et al., *Tissue Antigens* 46:86–95 (1995). The amplification products first are denatured to form single-stranded molecules. Chemical denaturation, e.g., with formamide, heat denaturation or enzymatic denaturation can be employed.

The denatured single-stranded amplification products are then separated electrophoretically under non-denaturing conditions. Preferably, the electrophoresis is conducted on a non-denaturing polyacrylamide gel, such as a 10% polyacrylamide buffered with tris-borate EDTA (TBE). Under these conditions, the single-stranded molecules assume conformations that are affected by the nucleotide sequences. It has been found that a difference in a single base can affect conformation sufficiently that an electrophoretic separation can be achieved. The amplification products may be visualized on the gel by any appropriate method, such as silver staining, ethidium bromide staining or Sybr™ green I nucleic acid stain available from Molecular Probes, Inc., Eugene, Oreg. 97402-0414 USA. Silver staining is preferred.

The nucleic acid amplification-SSCP procedures are fast and convenient and have been found to produce patterns characteristic of Rfp-Y and B gene haplotypes. As these patterns are developed for a wide range of commercial lines, a database may be created to allow breeders to correlate haplotypes with the particular desired disease resistance(s) and thereby select birds for breeding which have Rfp-Y and/or B haplotypes that are associated with resistance to diseases.

The invention is further illustrated by the following examples, which are not intended to be limiting.

EXAMPLE 1

Correlation of Rfp-Y Haplotype and Marek's Disease Resistance

Chickens. Chicks used in the challenge experiments were produced by parents from the stock in which the Rfp-Y system had been originally identified (Briles, W. E. et al., *Immunogenetics*, 37:408–414 (1993). B system haplotypes segregating in the stock were $B^{11}$ and $B^{19}$. The $R^{R9}$ haplotype ($B^{24r2}$ by standard international nomenclature) is one of the 12 B-F/B-G recombinant haplotypes preserved at Northern Illinois University, designated as $B^{R1}$ through $B^{R12}$. Typing with B-F and B-G specific alloantisera showed that $B^{R9}$ consists of $F^{24}$-$G^{23}$ (Briles, W. E. et al. *Animal Genetics*, 2:18 (1994)) with further evidence for B-$G^{23}$ found in the analysis of B-G proteins by two dimensional gel electrophoresis (Miller, M. M. et al. 1988).

B system genotypes among parents. Matings for the production of chicks to be challenged with MDV were designed so that each family would be expected to consist of $B^{11}/B^{11}$ and $B^{R9}/B^{11}$ genotypes in an expected 1:1 ratio. The chicks resulted from the mating of three sires of genotype $B^{R9}/B^{11}$ to seven females of the genotype $B^{11}/B^{11}$ and of six males of genotype $B^{11}/B^{11}$ to fifteen females of the genotype $B^{R9}/B^{11}$.

Rfp-Y system genotypes among parents. The primary objective in designing the matings to produce chicks for challenge with MDV was to obtain from each individual mating two Y genotypes among the progeny—a homozygote and a heterozygote having one allele in common. For example, a male of the genotype $Y^3/Y^3$ mated to a female of the genotype $Y^1/Y^3$ would be expected to produce progeny of the genotypes $Y^1/Y^3$ and $Y^3/Y^3$. The requirement that each mating be designated to produce in equal numbers of two Y genotypes was instituted to reduce the confounding of Y genotype performance of the challenged chicks with family structure. The gene frequencies for the $Y^1$, $Y^2$ and $Y^3$ among the 22 females were 0.39, 0.27, and 0.34, respectively, and among the 9 males were 0.17, 0.11, and 0.72, respectively. In addition to the restrictions regarding distribution of B and Rfp-Y among the parents, each male and female paired to produce chicks were from different families of the previous year.

Challenge of chicks with MDV. Matings were made by artificial insemination, eggs were labeled by mating code and shipped to the University of California at Davis by overnight freight for incubation and pedigree hatch. The chicks were double wing-banded to avoid accidental loss of identification and were reared on the floor in a clean environment. Feed and water were available ad libitum, and the chicks were observed at least once daily. Specific pathogen-free (SPF) eggs were obtained from flock RF2 maintained at HyVac Inc., Ames, IA, incubated, and hatched at the University of California at Davis. The chicks were placed unbanded in rooms with the chicks hatched from the experimental matings.

Virus and inoculation procedures. The pedigree-hatched chicks were challenged intra-abdominally with 500 plaque forming units of the RB1B strain of MDV (Schat, K. A. et al. *Avian Pathol.*, 11:593–605 (1982)). The RB1B virus was propagated in chick-kidney tissue culture cells at the University of California at Davis. The virus from the third or fourth passage was used for challenge. All SPF chicks received their challenge by contact-exposure to the intra-abdominally challenged chicks.

Blood collection and testing. Whole blood samples were collected in EDTA collection tubes and were analyzed for the B and Rfp-Y haplotypes of the individual birds. The haplotypes were determined by restriction fragment patterns displayed in Southern hybridizations of DNA digested with Bgl I restriction enzyme and hybridized with a B-LBII probe, as previously described (Briles, W. E. et al., *Immunogenetics*, 37:408–414 (1993). B types were distinguished by the presence of restriction fragments of approximately 4.0 and 4.4 kb.

Tissue collection and processing. Chicks were euthanized and the thymus, spleen, liver, kidney, lung, gonads, sciatic nerves and plexes, brachial nerves and plexes, bursa of Fabricius, heart, and any other affected tissues were collected for histological processing. Tissues were fixed in 10% neutral buffered formalin, imbedded in paraffin, sectioned at 6 μm, and stained with hematoxylin and eosin (Luna, L. G., *Manual of Histologic Staining Methods of the Armed Forces Institute of Pathology*, 3rd Ed., McGraw-Hill Book Co., New York, pp. 32–46 (1968)).

Experimental design. Replicate trials were conducted as follows: Trial 1: Incubation of two hundred pedigreed eggs resulted in 97 chicks; 86 of which completed the challenge test. At 5 days of age, the chicks were challenged and 10 one-day-old SPF chicks were added to the flock. Chicks were observed daily for clinical signs of Marek's disease ("MD") and post-mortem examinations were conducted on all dead birds. At 3 weeks of age, blood samples were collected for B and Y typing of individual chicks. The trial was terminated 75 days post-challenge (PC) and a gross necropsy examination was performed on all birds. Tissues were collected from all birds dying prior to termination and at termination for confirmation of MD by microscopic examination. In trial one, 7 out of 8 SPF control birds had gross and/or histologic evidence for MDV tumor formation.

Trial 2: Incubation of two hundred pedigreed eggs resulted in 87 chicks; 80 of which completed the challenge test. Challenge, blood collection, and handling were conducted as in Trial 1. Four SPF chicks were added to the flock on day 4 PC. The trial was terminated on day 75 PC. In trial 2 four out of four SPF control chicks had gross and/or histologic evidence of MDV tumor formation.

Statistical analysis. Logistic regression was used to investigate the joint dependence of tumor incidence on genotypes at both the B and Rfp-y systems. For the B system, a single dummy variable was created, para-meterizing the risk in $B^{R9}/B^{11}$ homozygotes. For the Rfp-Y system, the effect of the $Y^3$ haplotype was explored, because this is the most frequently occurring Rfp-Y haplotype in this genetic stock in which Rfp-Y was first recognized. This stock is several generations into the production of congenic lines for B system recombinant haplotypes and was otherwise without selection. Three models were compared for the effect of the $Y^3$ haplotype, denoted dominant, recessive and codominant. In the dominant model, $Y^3$ homozygotes and heterozygotes were combined and their risk estmated relative to non-$Y^3$ carriers. In the recessive model, $Y^3$ homozygotes are compared with the remaining birds, and in the codominant model, the risks for $Y^3$ homozygotes and heterozygotes were separately estimated, relative to non-$Y^3$ carriers. Likelihood ratio tests and Akaike's Information Criteria (AIC) were used to compare alternative models.

Results. Overall, MD was observed in 51 (30%) of the 168 birds on study. Table 1 shows the distribution of MD tumors tabulated by genotypes at the B and Rfp-Y systems.

regardless of the type of model used for the Rfp-Y system. Conditional on the B system included in the model, the recessive model for $Y^3$ fit the data better than the dominant of the codominant model, with $Y^3/Y^3$ homozygotes showing significantly higher incidence than birds with other genotypes combined (P<0.02). Additionally this model also predicts incidence for $B^{R9}/B^{11}$ heterozygotes to be 2.3 times higher than the incidence for $B^{11}/B^{11}$ homozygotes. In a subsequent analysis, a term was added to the model for the interaction between the B system and the recessively coded Rfp-Y system. This interaction was not found to be statistically significant (P=0.89).

TABLE 1

Incidence of Marek's Disease Tumors by Rfp-Y and B Genotype

| B Genotype | Rfp-Y Genotype | | | | | | |
|---|---|---|---|---|---|---|---|
| | 1/1 | 1/2 | 1/3 | 2/2 | 2/3 | 3/3 | Combined |
| $B^{11}/B^{11}$ | 13% (1/8) | 40% (2/5) | 11% (2/18) | 0% (0/5) | 23% (5/22) | 33% (13/39) | 24% (23/97) |
| $B^{09}/B^{11}$ | 38% (3/8) | 50% (1/2) | 50% (8/16) | 40% (2/5) | 12% (2/17) | 52% (12/23) | 39% (28/71) |
| Combined | 25% (4/16) | 43% (3/7) | 29% (10/34) | 20% (2/10) | 18% (7/39) | 40% (25/62) | 30% (51/168) |

TABLE 2

EXON 2 (α1 DOMAIN) SEQUENCES OF CHICKEN CLASS I GENES

| | | |
|---|---|---|
| BF-IV | AGCTCCATACCCTGCGGTACATCCAAACGGCGATGACGGATCCCGGCCCC | 50 |
| BF-I | AGCTCCATTCCCTGCGGTACGTCCATACGGCGATGACGGATCCCGGCCCC | 50 |
| YF-V | GGTCGCACTCCCTGCGCTACTTCCTGACCGGGATGACGGATCCCGGCCCC | 50 |
| YF-VI | GGTCGCACTCCCTGCGCTACTTCCTGACCGGGATGACGGATCCCGGCCCC | 50 |
| | Primer 72 | |
| BF-IV | GGGCAGCCGTGGTTCGTGACTGTGGGGTACGTG<u>GACGGGGAACTCTTCGT</u> | 100 |
| BF-I | GGGCTGCCGTGGTTCGTGGACGTGGGGTACGTGGACGGGGAACTCTTCGT | 100 |
| YF-V | GGGATGCCGCGGTTCGTGATCGTCGGGTACGTGGACGACAAAATCTTCGC | 100 |
| YF-VI | GGGATGCCGCGGTTCGTGATCGTCGGGTAC<u>GTGGACGACAAAATCTTCGG</u> | 100 |
| | Primer 75 | |
| BF-IV | <u>GC</u>ACTACAACAGCACCGCGCGGAGGTACGTGCCCCGCACCGAGTGGATAG | 150 |
| BF-I | GCACTACAACAGCACCGCGCGGAGGTACGTGCCCCGCACCGAGTGGATGG | 150 |
| YF-V | TACCTACAACAGTAA-GAGCAGGACTGCACAGCC--TATCGTGGAGAT-G | 146 |
| YF-VI | <u>T</u>ATCTACGACAGTAA-GAGCAGGACTGCACAGCC--CATCGTGGAGAT-G | 146 |
| BF-IV | CGGCCA-AGGCGGACCAGCAGTACTGGGATGCACAGACGCAGATCGGACA | 199 |
| BF-I | CGGCCA-ACACGGACCAGCAGTACTGGGATGGACAGACGCAGATCGGACA | 199 |
| YF-V | CTGCCGCAGGAGGACCAGGAGCACTGGGACACGCAGACCCAGAAGGCGCA | 196 |
| YF-VI | CTGCCGCAGGAGGACCAGGAGCACTGGGACGCGCAGACCCAGAAGGCCCA | 196 |
| | Primer 73 | |
| BF-IV | GGGCAATGAGCAGATTGACCGCGAGAACCTGGGCATAC<u>TGCAGCGGCGCT</u> | 249 |
| BF-I | GGGCAATGAGCGGAGTGTGGAAGTGAGCTTGAACACACTGCAGGAACGAT | 249 |
| YF-V | GGGCGGTGAGCGGGATTTTGACTGGAACCTGAACAGGCTGCCGGAACGCT | 246 |
| YF-VI | GGGCGGTGAGCGGGATTTTGACTGGTTCCTGAGCA<u>GGCTGCCGGAACGCT</u> | 246 |
| | Primer 76 | |
| BF-IV | <u>ACAACCAGA</u>CCGGCG 264 (SEQ ID NO: 2) | |
| BF-I | ACAACCAGACCGGCG 264 (SEQ ID NO: 1) | |
| YF-V | ACAACAAAAGTAAAG 261 (SEQ ID NO: 3) | |
| YF-VI | <u>ACAACAAAA</u>GTGGAG 261 (SEQ ID NO: 4) | |

There was significantly higher incidence in $B^{R9}/B^{11}$ birds (39.4%), compared with $B^{11}/B^{11}$ birds (23.7%, P=0.029), collapsing across Rfp-Y genotypes. The frequency of birds with respect to Rfp-Y genotypes shows that 37% of the birds are homozygous for $Y^3$, 40% are heterozygous for $Y^3$ and only 33% carry one of the remaining three genotypes. Incidence rates range from 18% for $Y^2/Y^3$ carriers to 43% for $Y^1/Y^2$ carriers, although the latter estimate is based on only seven birds. With respect to the $Y^3$ haplotype, the highest incidence is observed for $Y^3/Y^3$ homozygotes (40%).

Based on the logistic regression analysis, the B system was significantly associated with tumor incidence (P<0.02),

EXAMPLE 2

PCR-SSCP Determination of Rfp-Y and B-F Haplotypes

The PCR-SSCP typing tests are based on sequences coding for the α1 domains of Class I molecules, B-FI, B-FIV, Y-FV and Y-FVI identified as SEQ. ID NO. 1, SEQ. ID NO. 2, SEQ ID NO. 3 and SEQ ID NO. 4 respectively. See Table 2. Two primer sets were used. Primers 72 and 73, the primers for the sense and antisense strands of the B-F gene segments, are identified as SEQ ID NO. 5 and SEQ ID NO. 6, respectively. Primers 75 and 76, the primers for the sense and antisense strands of Y-F gene segments, are identified as SEQ ID NO. 7 and SEQ ID NO. 8, respectively. The primer sequences are set forth in Table 3 below.

The conditions for PCR amplification of these 174 base pair segments were as follows:
PCR reaction mixture:
  5 µl of Taq DNA Polymerase Buffer 10× (Perkin Elmer Corp.)
  1 µl dNTP mixture (DATP, dCTP, dGTP, dTTP, 10 mM each, Boehringer)
  1 µl primer 72 or 75 (20 µM)
  1 µl primer 73 or 76 (20 µM)
  100 ng genomic DNA
  qsp 49 µl with water.

Samples were denatured for 5 minutes at 95° C. and were conserved on ice. One microliter (1 U) of Taq DNA polymerase diluted 5× (Perkin Elmer 5 U/µl) was added. and the samples were covered with 30 µl of white mineral oil (Mallinckrodt). Thirty cycles of PCR were performed with each cycle consisting of denaturation for 45 seconds at 95° C., annealing for 45 seconds at 63° C. and elongation for 45 seconds at 72° C., followed by one cycle of PCR with elongation for 5 minutes at 72° C.

The PCR was monitored by agarose gel electrophoresis as follows: A 1.5% agarose (FMC Bioproducts) electrophoresis gel in tris-borate EDTA ("TBE") 1× buffer (89 mM Tris-borate (Fisher Biotech), 89 mM boric acid (Mallinckrodt) and 2 mM EDTA (Mallinckrodt)) was prepared. Five to ten microliters of PCR products were loaded onto the gel with 1 µl dye 10× (0.5% bromophenol blue (Sigma), 0.5% Xylene cyanol (Gibco-BRL), 40% (w/v) sucrose (IBI) in water). Electrophoresis was run in TBE 1× at 120 V for 45 minutes. The gel was stained with ethidium bromide (10 µg/ml, Sigma) for 5 minutes. PCR products were visualized with ultraviolet light.

SSCP electrophoresis of the PCR products was conducted as follows:

A 10% polyacrylamide gel in TBE (0.5×) was prepared by combining (for a 6 ml gel) 3.7 ml water, 300 µl TBE 10×, 2 ml acrylamide (11.4 g acrylamide (Boehringer) plus 0.6 g bis-acrylamide (BioRad) in 40 ml water), 3 µl TEMED (N,N,N',N'-tetramethylethylenediamine) (Sigma) and 30 µl ammonium persulfate 10% (BioRad).

PCR products (1 to 3 µl) were denatured for 5 minutes at 80° C. with 10 µl dye 1× (300 µl formamide (Fisher) plus 3 µl dye 10×). The denatured PCR products were loaded onto the gel. Electrophoresis was run in TBE 0.5× at 200 V for 1 hour 45 minutes. Conditions for electrophoresis may be varied. In particular, longer electrophoresis times at lower voltage can produce clearer results. The gel was fixed by treating for 20 minutes with 50 ml. of: methanol 50% (v/v) (Mallinckrodt), acetic acid 10% (v/v) (Mallinckrodt), fixative enhancer concentrate 10% (v/v) (BioRad Silver Stain Plus Kit) in water 30% (v/v). The fixed gel was washed twice with water for 10 minutes. A staining solution (BioRad Silver Stain Plus Kit) was prepared by combining the following: 25 ml water, 2.5 ml Silver Complex Solution, 2.5 ml Reaction Moderator Solution, 2.5 ml Image Development Reagent and 12.5 ml Development Accelerator Solution. The gel was stained with this solution for 10 minutes, was fixed with 25 ml 5% acetic acid for 15 minutes and was dried in cellophane.

Figure 2:
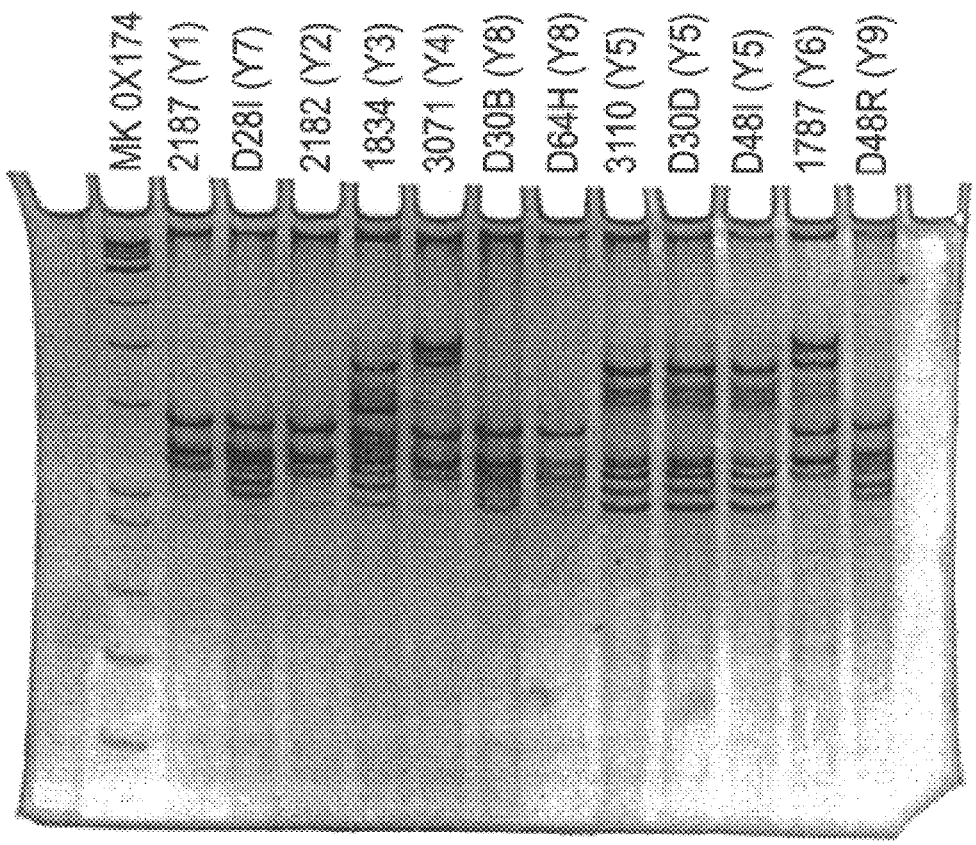
FIG. 2 is a photograph of a gel showing the SSCP electrophoretic pattern of polymerase chain reaction products associated with different Mhc Y Class I genotypes as indicsated. MKϕX174=molecular weight markers.

The PCR yielded products of the expected size (174 bp). The resulting SSCP patterns for seven B system haplotypes, $B^Q$, $B^2$, $B^{12}$, $B^{15}$, $B^{18}$, $B^{21}$ and $B^{24}$, and nine Rfp-Y haplotypes, $Y^1$ to $Y^9$, are shown in FIGS. 1–2. A 174 bp non-denatured PCR amplification product is shown in the ninth lane at the left of the FIG. 1. After denaturation, electrophoresis and staining, these PCR amplification products give different patterns of bands which are specific for the sequences amplified and consequently specific for the haplotype from which they originate. B system patterns produced with primers OL72BF and RV73BF are presented on the gel provided in FIG. 1 and Rfp-Y systems patterns produced with primers OL75YF and RV76YF are presented on the gel provided in FIG. 2. Thus, the PCR-SSCP method provides a fast and efficient means for determining the Rfp-Y and B-F haplotypes.

TABLE 3

Sequence (5'→3') of Primers Useful for Mhc Genotyping

| Primer OL72BF | gacggggaactcttcgtgca | (SEQ ID NO: 5) |
| Primer RV73BF | tctggttgtagcgccgctgca | (SEQ ID NO: 6) |
| Primer OL75YF | gtggacgacaaaatcttcggta | (SEQ ID NO: 7) |
| Primer RV76YF | tttgttgtagcgttccggcagcc | (SEQ ID ND: 8) |
| Primer OL246BF | gagctccatacctgcgg | (SEQ ID NO: 9) |
| Primer RV247BF | ggtctggttgtagcgccg | (SEQ ID NO: 10) |
| Primer OL27BG | gggagaacagaactgctcagg | (SEQ ID NO: 11) |
| Primer RV24BG | cacctccaggtccaccacagc | (SEQ ID NO: 12) |
| Primer OL56BL | gagtgccactacctgaacggcaccgagcgg | (SEQ ID NO: 13) |
| Primer RV69BL | gctcctctgcaccgtgaagga | (SEQ ID NO: 14) |
| Primer OL277YF | ggtcgcactccctgcgc | (SEQ ID NO: 15) |
| Primer RV278YF | acttttgttgtagcgttccg | (SEQ ID NO: 16) |
| Primer RV280BL | tcctctgcaccgtgaagg | (SEQ ID NO: 17) |
| Primer OL283BL | gtggacggggaactcttc | (SEQ ID NO: 18) |
| Primer OL284BL | ctgcccgcagcgttcttc | (SEQ ID NO: 19) |

EXAMPLE 3

PCR-SSCP Determination of Mhc Class I Haplotype

Primers OL246BF and RV247BF encompass a segment of B Class I exon 2 sequences and enable SSCP analysis of a larger PCR product of a calculated 261 bp. The sequences of primers OL246BF (SEQ ID NO. 9) and RV247BF (SEQ ID NO: 10) are provided in Table 3. The PCR mixture included 5 µl 10× Taq polymerase buffer, 1 µl dNTP mixture (dATP, dCTP, dGTP and dTTP; 10 mM each; Bochringer), 1 µl primer OL246BF (20 µm), 1 µl primer RV247BF (20 µm), 100 ng genomic DNA and distilled water to a 50 µl final volume. Samples were denatured for 5 minutes at 95° C. and placed on ice. One microliter (1U) Taq DNA polymerase (Amplitaq, Perkin Elmer) diluted 5× (Perkin Elmer 5u/ml) was added. Thirty-five cycles of PCR were performed in a Stratagene Robocycler™ with Hot Top feature. Each cycle consisted of denaturation for 45 seconds at 95° C., annealing for 45 seconds at 60° C. and elongation for 45 seconds at 72° C. The final cycle was followed by 5 minutes at 72° C.

Figure 3:
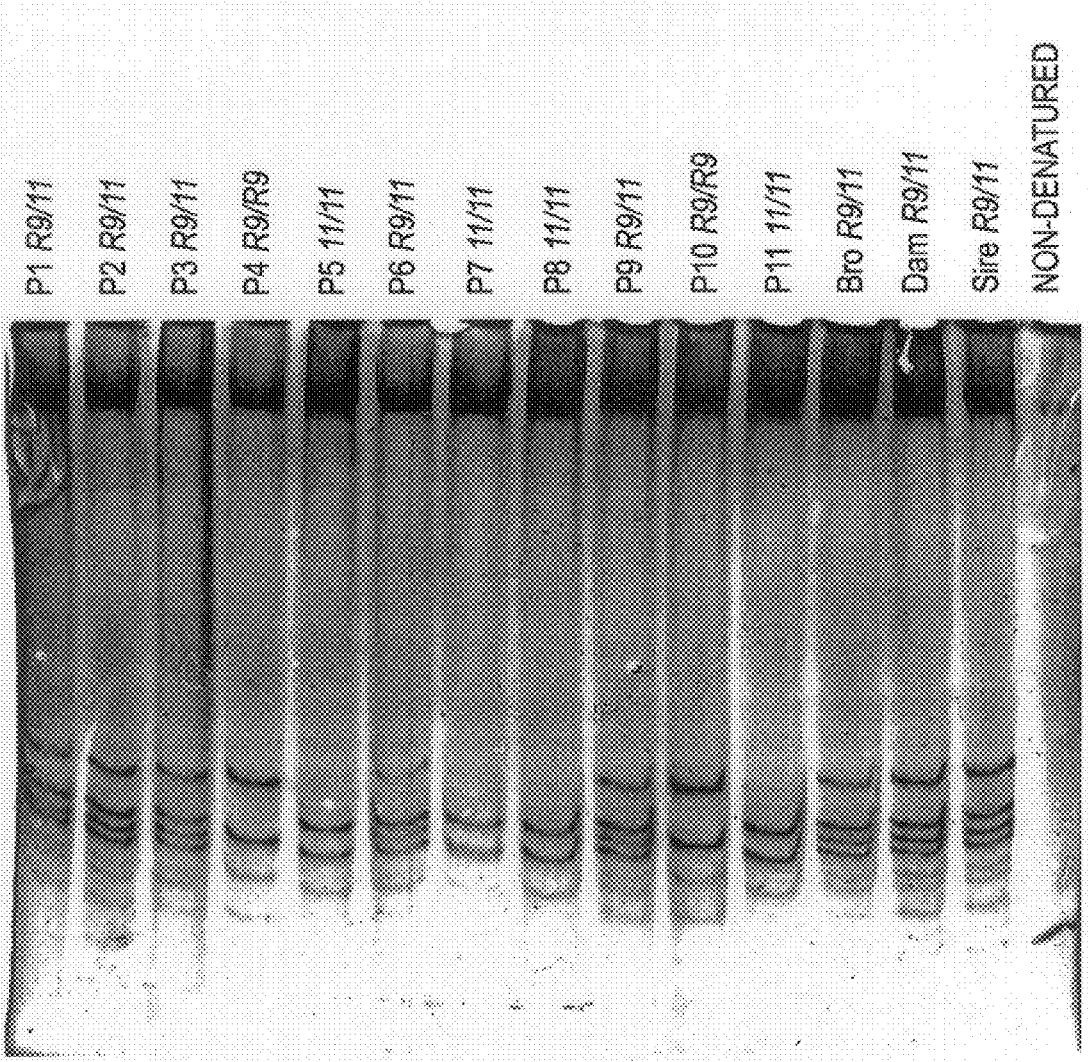
FIG. 3 is a photograph of a gel showing the SSCP electrophoretic pattern of polymerase chain reaction products associated with different Mhc B Class I genotypes as indicated.

The reaction was monitored by agarose gel electrophoresis on a TBE 1.5% agarose gel; SSCP electrophoresis was carried out in a 10% polyacrylamide gel in 0.5× TBE. One to 3 μl of PCR product was denatured for 5 minutes at 80° C. with 10 μl dye 1× (300 μl formamide with 3 μl dye 10×). The denatured product was placed on ice and then loaded onto the polyacrylamide gel. The samples were electrophoresed for about 1.75 hours in 0.5× TBE at 200V. The gel was fixed and stained with a BioRad Silver Stain Kit. Briefly, the gels were fixed by treating for 20 minutes with fixative enhancer solution (methanol 50% (v/v), acetic acid 10% (v/v) and Fixative Enhancer Concentrate 10% (v/v) from the BioRad Silver Stain Plus Kit made up in distilled water (30% (v/v)) The fixed gel was washed twice with distilled water for 10 minutes. A staining solution from BioRed Silver Stain Plus Kit was prepared by combining the following: 17.5 ml distilled water, 2.5 ml Silver Complex Solution, 2.5 ml Reaction Moderator Solution, 2.5 ml Image Development Reagent and 12.5 ml Development Accelerator Solution. Gels were stained with this solution for 10–15 minutes, fixed for 15 minutes in 5% acetic acid and dried between sheets of cellophane in a drying frame. Digitized images of the gels were made with a scanner. The results are shown in FIG. 3. The samples were taken from a fully pedigreed family including sire, dam, brother to the dam and eleven progeny.

EXAMPLE 4

PCR-SSCP Determination of Mhc B-G Genotype

Figure 4:
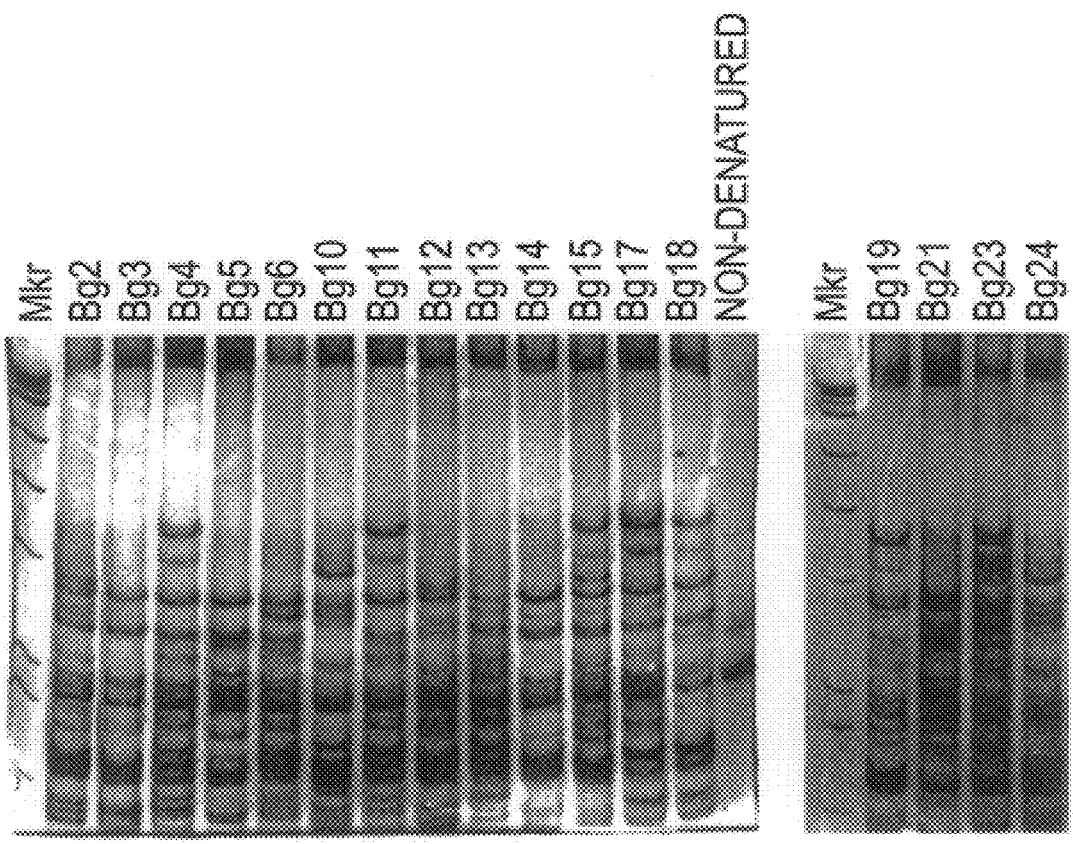
FIG. 4 is a photograph of gels showing the SSCP electrophoretic pattern of polymerase chain reaction products associated with different Mhc B-G genotypes as indicated. Mkr=molecular weight markers; Non-denat. indicates that the PCR amplification product was not heat denatured before loading for gel electrophoresis.

PCR-SSCP was carried out as in Example III except that an annealing temperature of 65° C. was used and primers OL27BG and RV24BG (SEQ ID NO: 11 and 12, respectively, see Table 3) were substituted for primers OL246BF and RV247BF. Additionally, the samples were electrophoresed for 2 hours rather than 1.75 hours. Results are given in FIG. 4. Samples were from birds serologically defined as homozygous for Mhc B haplotypes.

EXAMPLE 5

PCR-SSCP Determination of Mhc B Class IIβ Genotype

Figure 5B:
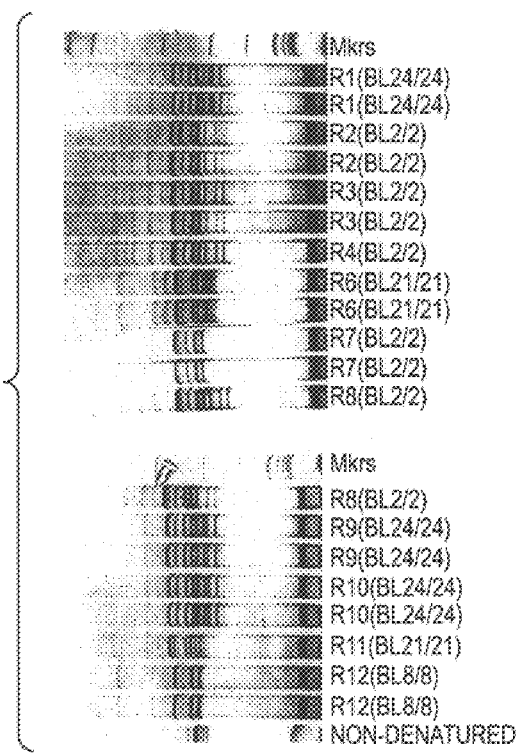
FIG. 5B shows analysis of birds having serologically defined recombinant haplotypes.
Figure 5A:
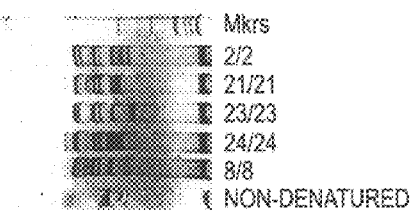

PCR-SSCP was carried out as in Example III except that an annealing temperature of 65° C. was used and primers OL56BL and RV69BL (SEQ ID NOS: 13 and 14, respectively, see Table 3) were substituted for primers OL246BF and RV247BF. Results are given in FIG. 5. Analysis includes DNA from five birds bearing five of the standard Mhc B haplotypes (FIG. 5A) and 20 samples from birds bearing serologically-defined recombinant haplotypes (FIG. 5B).

EXAMPLE 6

PCR-SSCP Determination of Rfp-Y Class I Genotype

Figure 6:
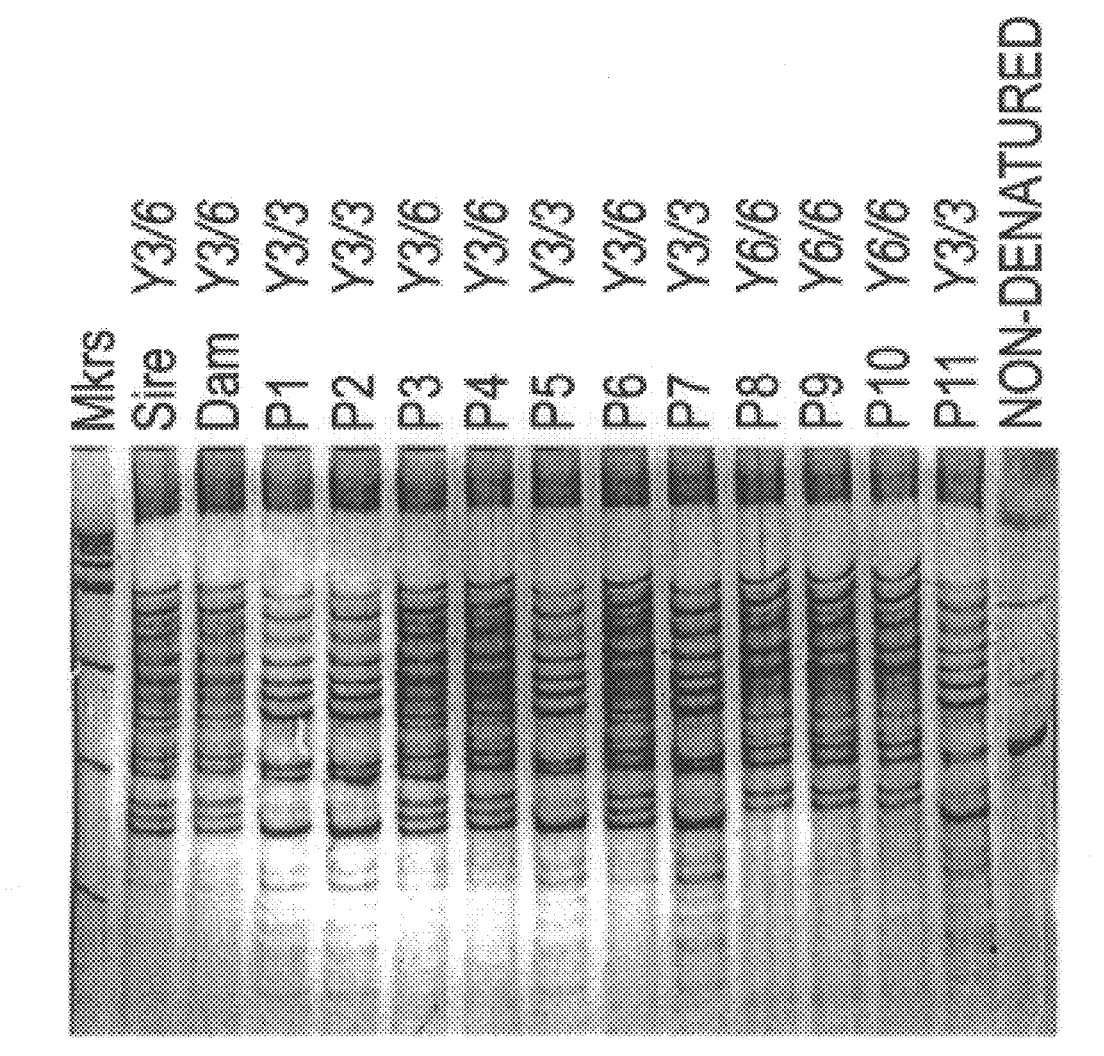

PCR-SSCP was carried out as in Example III except that primers OL277YF and RV278YF (SEQ ID NOS: 15 and 16, respectively, see Table 3) were substituted for primers OL246BF and RV247BF. Results are given in FIG. 6. Sample haplotypes assigned by restriction fragment patterns are listed across the top. The samples were taken from a full pedigreed family, including sire, dam and 11 progeny.

EXAMPLE 7

PCR-SSCP Determination of Mhc B Class I Genotyping

Figure 7:
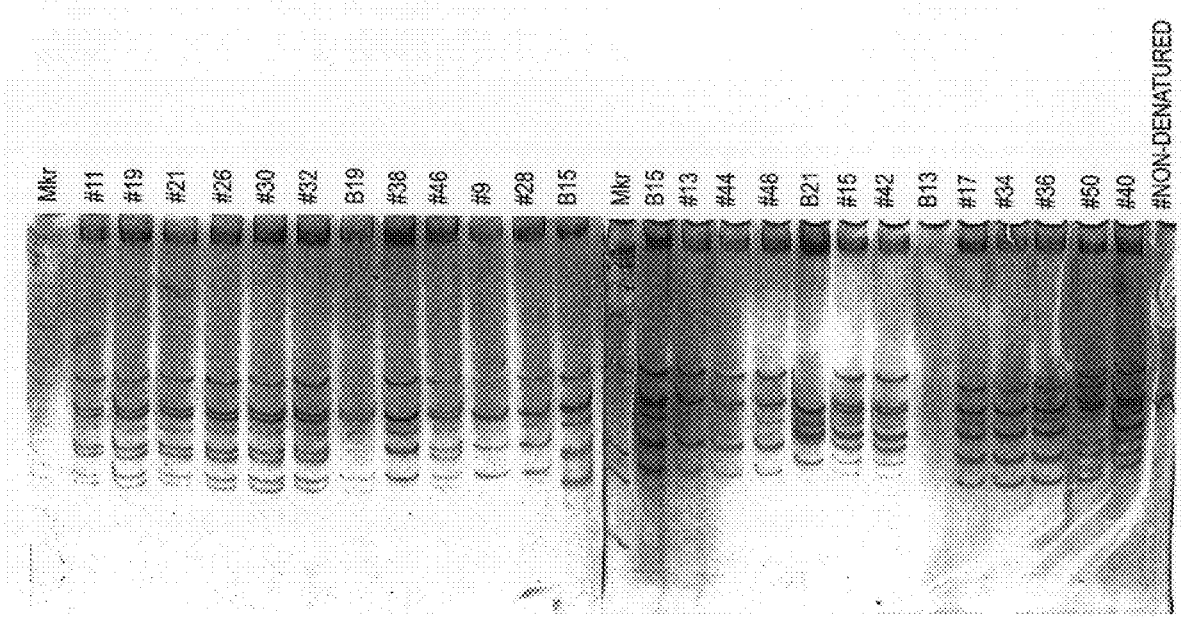
FIG. 7 is a photograph of a gel showing the SSCP electrophoretic pattern of polymerase chain reaction products associated with different Mhc B Class I genotypes. Mkr=molecular weight markers. The numbered samples were derived from birds of unknown haplotypes, grouped together and analyzed in comparison with the indicated known haplotypes.

PCR-SSCP was carried out as in Example III except that primers OL283BF and RV73BF (SEQ ID NOS: 18 and 6, respectively, see Table 3) were substituted for primers OL246BF and RV247BF. Results are given in FIG. 7. Birds bearing unknown B haplotypes were grouped together based on previously determined restriction fragment pattens and analyzed in comparison with the SSCP patterns of known B haplotypes. Most of the birds appear to be heterozygous with portions of the SSCP patterns identical to those provided by birds of homozygous for standard B haplotypes.

EXAMPLE 8

PCR-SSCP Determination of Mhc B Class IIβ Genotype

Figure 8:
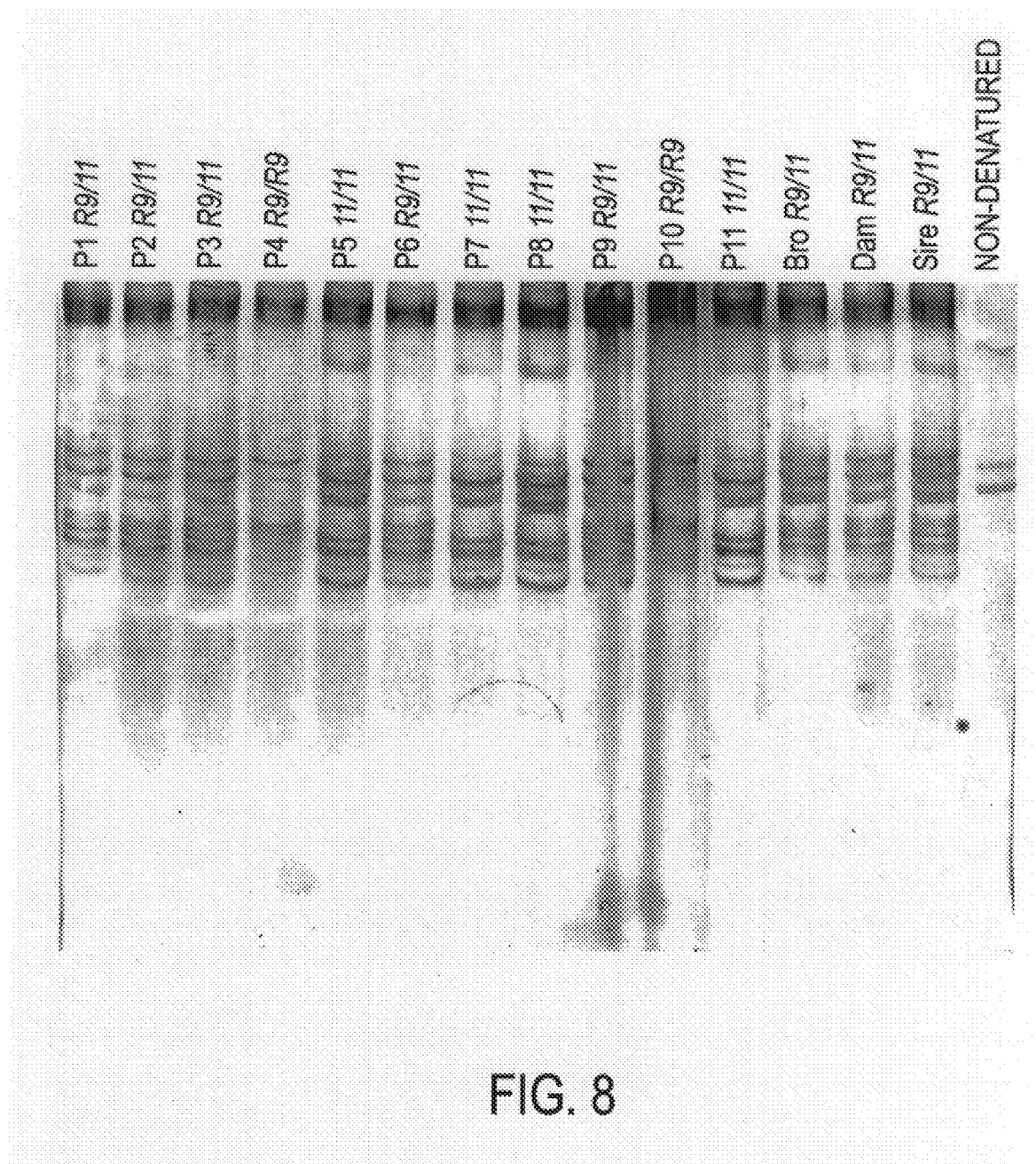
FIG. 8 is a photograph of a gel showing the SSCP electrophoretic pattern of polymerase chain reaction products associated with different Mhc B Class II genotypes as indicated.

PCR-SSCP was carried out as in Example III except that primers OL284BL and RV280BL (SEQ ID NOS: 19 and 17, respectively, see Table 3) were substituted for primers OL246BF and RV247BF. Results are given in FIG. 8. The samples were taken from a fully pedigreed family including sire, dam, brother to the dam and eleven progeny.

What is claimed is:

1. A primer selected from the group consisting of SEQ ID NO: 17, and SEQ ID NO: 19.

2. A method for determining the Mhc genotype of a chicken, which comprises:

(a) obtaining a sample of nucleic acid from said chicken which contains a region having a sequence corresponding to an Rfp-Y, B-F, B-L or B-G region of the genome which is subject to allelic variation;

(b) amplifying said region using the polymerase chain reaction using primers that amplify a region of the Rfp-Y or B system, wherein said primers have the nucleotide sequences set forth in SEQ ID NOS:19 and 17; to generate amplification products (c) denaturing said amplification products to produce denatured amplification products;

(d) subjecting said denatured amplification products to non-denaturing electrophoretic separation to produce an electrophoresis pattern that is characteristic of the Rfp-Y, B-F, B-L or B-G region genotype of said chicken; and (e) comparing said electrophoresis pattern to at least one electrophoresis pattern produced by a standard nucleic acid sample obtained, amplified, denatured and subjected to electrophoretic separation according to steps (a) through (d), wherein said standard nucleic acid is obtained from a chicken of known Rfp-Y, B-F, B-L or B-G genotype.

* * * * *

UNITED STATES PATENT AND TRADEMARK OFFICE
CERTIFICATE OF CORRECTION

PATENT NO.    : 6,667,164 B1
DATED         : December 23, 2003
INVENTOR(S)   : Miller et al.

It is certified that error appears in the above-identified patent and that said Letters Patent is hereby corrected as shown below:

Column 3,
Line 30, "indicsated" should read -- indicated --;

Columns 9 and 10,
Table 1, third row, "$B^{09}/B^{11}$" should read -- $B^{R9}/B^{11}$ --;

Column 11,
Line 6, "DATP" should read -- dATP --;

Column 12,
Line 57, "Bochringer" should read -- Boehringer --.

Signed and Sealed this

Thirteenth Day of July, 2004

JON W. DUDAS
*Acting Director of the United States Patent and Trademark Office*

SEQUENCE LISTING

<160> NUMBER OF SEQ ID NOS: 19

<210> SEQ ID NO 1
<211> LENGTH: 264
<212> TYPE: DNA
<213> ORGANISM: Gallus sp.

<400> SEQUENCE: 1

```
agctccattc cctgcggtac gtccatacgg cgatgacgga tcccggcccc gggctgccgt      60
ggttcgtgga cgtggggtac gtggacgggg aactcttcgt gcactacaac agcaccgcgc     120
ggaggtacgt gccccgcacc gagtggatgg cggccaacac ggaccagcag tactgggatg     180
gacagacgca gatcggacag ggcaatgagc ggagtgtgga agtgagcttg aacacactgc     240
aggaacgata caaccagacc ggcg                                             264
```

<210> SEQ ID NO 2
<211> LENGTH: 264
<212> TYPE: DNA
<213> ORGANISM: Gallus sp.

<400> SEQUENCE: 2

```
agctccatac cctgcggtac atccaaacgg cgatgacgga tcccggcccc gggcagccgt      60
ggttcgtgac tgtggggtac gtggacgggg aactcttcgt gcactacaac agcaccgcgc     120
ggaggtacgt gccccgcacc gagtggatag cggccaaggc ggaccagcag tactgggatg     180
cacagacgca gatcggacag ggcaatgagc agattgaccg cgagaacctg gcatactgc      240 agcggcgcta caaccagacc ggcg                                            264
```

<210> SEQ ID NO 3
<211> LENGTH: 261
<212> TYPE: DNA
<213> ORGANISM: Gallus sp.

<400> SEQUENCE: 3

```
ggtcgcactc cctgcgctac ttcctgaccg ggatgacgga tcccggcccc gggatgccgc      60
ggttcgtgat cgtcgggtac gtggacgaca aaatcttcgc tacctacaac agtaagagca     120
ggactgcaca gcctatcgtg gagatgctgc cgcaggagga ccaggagcac tgggacacgc     180
agacccagaa ggcgcagggc ggtgagcggg attttgactg gaacctgaac aggctgccgg     240
aacgctacaa caaaagtaaa g                                               261
```

<210> SEQ ID NO 4
<211> LENGTH: 261
<212> TYPE: DNA
<213> ORGANISM: Gallus sp.

<400> SEQUENCE: 4

```
ggtcgcactc cctgcgctac ttcctgaccg ggatgacgga tcccggcccc gggatgccgc      60
ggttcgtgat cgtcgggtac gtggacgaca aaatcttcgg tatctacgac agtaagagca     120
ggactgcaca gcccatcgtg gagatgctgc cgcaggagga ccaggagcac tgggacgcgc     180
agacccagaa ggcccagggc ggtgagcggg attttgactg gttcctgagc aggctgccgg     240
aacgctacaa caaaagtgga g                                               261
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer for
    SSCP analysis of Mhc B-F genotype of fowl

<400> SEQUENCE: 5

```
gacggggaac tcttcgtgca                                                  20
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer for
    SSCP analysis of Mhc B-F genotype of fowl

<400> SEQUENCE: 6

```
tctggttgta gcgccgctgc a                                              21
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer for
      SSCP analysis of Mhc Y-F  genotype of fowl

<400> SEQUENCE: 7

```
gtggacgaca aaatcttcgg ta                                             22
```

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer for
      SSCP analysis of Mhc Y-F genotype of fowl

<400> SEQUENCE: 8

```
tttgttgtag cgttccggca gcc                                            23
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer for
      SSCP analysis of Mhc B class I genotype of fowl

<400> SEQUENCE: 9

```
gagctccata ccctgcgg                                                  18
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Primer for
      SSCP analysis of Mhc B class I genotype of fowl

<400> SEQUENCE: 10

```
ggtctggttg tagcgccg                                                  18
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer for
      SSCP analysis of Mhc B-G genotype of fowl

<400> SEQUENCE: 11

```
gggagaacag aactgctcag g                                              21
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer for
      SSCP analysis of Mhc B-G genotype of fowl

<400> SEQUENCE: 12

```
cacctccagg tccaccacag c                                              21
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer for
      SSCP analysis of Mhc B class II-beta genotype of
      fowl

<400> SEQUENCE: 13
gagtgccact acctgaacgg caccgagcgg                                    30

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer for
      SSCP analysis of Mhc B class II-beta genotype of
      fowl

<400> SEQUENCE: 14
gctcctctgc accgtgaagg a                                             21

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Primer for
      SSCP analysis of Rfp-Y genotype of fowl

<400> SEQUENCE: 15
ggtcgcactc cctgcgc                                                  17

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer for
      SSCP analysis of Rfp-Y genotype of fowl

<400> SEQUENCE: 16
acttttgttg tagcgttccg                                               20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer for
      SSCP analysis of Mhc B Class II-beta genotype of
      fowl

<400> SEQUENCE: 17
tcctctgcac cgtgaagg                                                 18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer for
      SSCP analysis of Mhc B-F genotype of fowl

<400> SEQUENCE: 18

```
gtggacgggg aactcttc                                              18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Primer for
      SSCP analysis of Mhc B class II-beta genotype of
      fowl

<400> SEQUENCE: 19
ctgcccgcag cgttcttc                                              18
```